US006673352B1

(12) United States Patent
Donahoe et al.

(10) Patent No.: US 6,673,352 B1
(45) Date of Patent: Jan. 6, 2004

(54) USE OF MULLERIAN INHIBITING SUBSTANCE FOR TREATING EXCESS ANDROGEN STATES

(75) Inventors: Patricia K. Donahoe, Boston, MA (US); Jose Teixeira, Boston, MA (US); Eric Fynn-Thompson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/662,341

(22) Filed: Sep. 14, 2000

Related U.S. Application Data
(60) Provisional application No. 60/153,674, filed on Sep. 14, 1999, and provisional application No. 60/153,940, filed on Sep. 15, 1999.

(51) Int. Cl.[7] .................. A61K 39/00; A61K 38/00; G01N 33/567; C07K 14/00
(52) U.S. Cl. .................. 424/198.1; 435/7.21; 530/350; 530/324; 514/2
(58) Field of Search ................ 514/2; 530/350, 530/324; 435/7.21; 424/198.1

(56) References Cited

U.S. PATENT DOCUMENTS

| | | | |
|---|---|---|---|
| 4,404,188 A | 9/1983 | Donahoe et al. | 424/105 |
| 4,487,833 A | 12/1984 | Donahoe et al. | 435/172.2 |
| 4,753,794 A | 6/1988 | Donahoe | 424/85 |
| 5,010,055 A | 4/1991 | Donahoe | 514/8 |
| 5,011,687 A | 4/1991 | Donahoe et al. | 424/559 |
| 5,110,904 A | * 5/1992 | Haviv et al. | |
| 5,198,420 A | 3/1993 | Donahoe et al. | 424/85.8 |
| 5,310,880 A | 5/1994 | Donahoe et al. | 530/395 |
| 5,359,033 A | 10/1994 | Cate et al. | 530/350 |
| 5,427,780 A | 6/1995 | Cate et al. | 424/85.1 |
| 5,484,768 A | 1/1996 | Donahue et al. | 514/2 |
| 5,538,892 A | 7/1996 | Donahoe et al. | 435/240.2 |
| 5,547,854 A | 8/1996 | Donahoe et al. | 435/69.1 |
| 5,661,126 A | 8/1997 | Donahoe et al. | 514/12 |
| 5,906,979 A | * 5/1999 | Allan | |
| 5,912,224 A | 6/1999 | Donahoe et al. | 514/2 |

FOREIGN PATENT DOCUMENTS

| | | |
|---|---|---|
| WO | WO 89/06695 | 7/1989 |
| WO | WO 95/16709 | 6/1995 |

OTHER PUBLICATIONS

Shaw, M.A. et al., "Aminoglutethimide and Ketoconazole: Historical Perspectives and Future Projects," *J. Steroid Biochem.* 31:137–146, Pergamon Press plc (1988).

Sonino, N., "The Use of Ketoconazole as an Inhibitor of Steroid Production," *New England J. Med.* 317:812–818, The Massachusetts Medical Society (1987).

Barrie, S.E. et al., "Biochemistry and Pharmacokinetics of Potent Non–steroidal Cytochrome $P450_{17\alpha}$ Inhibitors," *J. Steroid Biochem. Molec. Biol.* 60:347–351, Elsevier Science Ltd. (1997).

Nnane, I.P. et al., "Inhibition of Androgen Synthesis in Human Testicular and Prostatic Microsomes and in Male Rats by Novel Steroidal Compounds," *Endocrinol.* 140:2891–2897, The Endocrine Society (Jun. 1999).

International Search Report for International Application No. PCT/US00/25094, mail Jan. 4, 2001.

*J. Cell. Biochem.* (Supplement 12A):183, UCLA Symposia on Molecular & Cellular Biology, Alan R. Liss, Inc. (1988).

*J. Cell. Biochem.* (Supplement 16B):123, Keystone Symposia on Molecular & Cellular Biology, Wiley–Liss, Inc. (1992).

*J. Cell. Biol.* 115(3, Part 2):276a, Rockefeller University Press (1991).

Baarends, W.M. et al., "A novel member of the transmembrane serine/threonine kinase receptor family is specifically expressed in the gonads and in mesenchymal cells adjacent to the mülllerian duct," *Development* 120:189–197, The Company of Biologists Limited (1994).

Baker, M.L. and Hutson, J.M., "Serum Levels of Mullerian Inhibiting Substance in Boys throughout Puberty and in the First Two Years of Life," *J. Clin. Endocrinol. Metabol.* 76:245–247, The Endocrine Society (1993).

Bardin, C.W. et al., "Androgens," in *Reproductive Endocrinology, Surgery and Technology*, vol. 1, Adashi, E.Y. et al., eds., Lippincott–Raven, Philadelphia, pp. 505–525 (1995).

Behringer, R.R. et al., "Abnormal sexual development in transgenic mice chronically expressing Müllerian inhibiting substance," *Nature* 345:167–170, Macmillan Journals (1990).

Behringer, R.R. et al., "Müllerian–Inhibiting Substance Function during Mammalian Sexual Development," *Cell* 79:415–425, Cell Press (1994).

Cate, R.L. et al., "Isolation of the Bovine and Human Genes for Müllerian Inhibiting Substance and Expression of the Human Gene in Animal Cells," *Cell* 45:685–698 (1986).

(List continued on next page.)

Primary Examiner—Yvonne Eyler
Assistant Examiner—Janet L. Andres
(74) Attorney, Agent, or Firm—Sterne, Kessler, Goldstein & Fox P.L.L.C.

(57) ABSTRACT

The present invention provides a method of treating a condition or disease characterized by an excess of one or more androgens, the method comprising administering an effective amount of MIS protein or nucleic acid encoding MIS to a patient. The present invention also provides a method of decreasing the level of one or more androgens to a level below the normal level, the method comprising administering an effective amount of MIS protein or nucleic acid encoding MIS to a patient. The methods of the present invention are particularly well-suited for the treatment of prostatic cancer, polycystic ovarian disease, benign prostatic hypertrophy, and precocious puberty.

15 Claims, 6 Drawing Sheets

OTHER PUBLICATIONS

Cate, R.L. et al., "Development of Mullerian Inhibiting Substance as an Anti-cancer Drug," *Cold Spring Harbor Symposia on Quantitative Biology*, vol. LT:641–647, Cold Spring Harbor Laboratory (1986).

Chin, T. et al., "Human Müllerian Inhibiting Substance Inhibits Tumor Growth in Vitro and in Vivo," *Cancer Res.* 51:2101–2106, American Association for Cancer Research (1991).

Crowley, W.F. et al., "Neuroendocrine & Gonadal Control Of Male Reproduction," application for National Institute of Child Health and Human Development grant No. 2. U54 HD–28138–10 (Apr. 1, 2000 or later).

di Clemente, N. et al., "Cloning, Expression, and Alternative Splicing of the Receptor for Anti–Müllerian Hormone," *Mol. Endocrinol.* 8:1006–1020, The Endocrine Society (1994).

Donahoe, P.K. et al., "A Graded Organ Culture Assay for the Detection of Mullerian Inhibiting Substance," *J. Surg. Res.* 23:141–148, Academic Press, Inc. (1977).

Donahoe, P.K. et al., "Mullerian Inhibiting Substance Inhibits Growth of a Human Ovarian Cancer in Nude Mice," *Ann. Surg.* 194:472–480, J.B. Lippincott Company (1981).

Donahoe, P.K., "Müllerian Inhibiting Substance in Reproduction and Cancer," *Mol. Reproduct. Develop.* 32:168–172, Wiley–Liss, Inc. (1992).

Donahoe, P.K. et al., "MIS Receptors–Novel Serine/Threonine Kinase Components," application for National Institute of Child Health and Human Development grant No. 2 R01 HD–32112–06A1 (Jan. 15, 2000 or later).

Fuller, Jr., A.F. et al., "Mullerian Inhibiting Substance Reduction of Colony Growth of Human Gynecologic Cancers in a Stem Cell Assay," *Gynecol. Oncol.* 22:135–148, Academic Press, Inc. (1985).

Fynn–Thompson, E., "Müllerian Inhibiting Substance Regulates Steroidogenesis in Rodent Leydig Tumor Cell Lines," Slides Presented at Harvard Medical School Prematriculation Summer Program Presentation, 13 pages (Aug. 1998).

Hudson, P.L. et al., "An Immunoassay to Detect Human Mullerian Inhibiting Substance in Males and Females during Normal Development," *J. Clin. Endocrinol. Metabol.* 70:16–22, The Endocrine Society (1990).

Josso, N. et al., "Anti–Müllerian Hormone: The Jost Factor," in Recent Progress in Hormone Research, vol. 48, Bardin, C.W., eds., Academic Press, Inc., New York, NY, pp. 1–59 (1993).

Josso, N. et al., "Anti–Müllerian hormone in early human development," *Early Hum. Dev.* 33:91–99, Elsevier Scientific Publishers Ireland Ltd. (1993).

Jost, P.A., "Recherches Sur La Differenciation Sexuelle De L Embryon De Lapin," *Archives D'Anatomie Microscopique et de Morphologie Expérimentale* 36:271–315 (1946).

Kendall, S.K. et al., "Targeted disruption of the pituitary glycoprotein hormone α–subunit produces hypogonadal and hypothyroid mice," *Genes Dev.* 9:2007–2019, Cold Spring Harbor Laboratory Press (1995).

Kim, J.H. et al., "The Inhibitory Effects of Müllerian–Inhibiting Substance on Epidermal Growth–Factor Induced Proliferation and Progesterone Production of Human Granulosa–Luteal Cells," *J. Clin. Endocrinol. Metabol.* 75:911–917, The Endocrine Society (1992).

Kretzschmar, M. and Massagué, J., "SMADs: mediators and regulator of TGF–β signaling," *Curr. Opin. Genet. Develop.* 8:103–111, Current Biology Ltd. (Feb. 1998).

Kurian, M.S. et al., "Cleavage of Müllerian Inhibiting Substance Activates Antiproliferative Effects in Vivo," *Clin. Cancer Res.* 1:343–349, American Association for Cancer Research (1995).

Lane, A.H. and Donahoe, P.K., "New insights into Mullerian inhibiting substance and its mechanism of action," *J. Endocrinol.* 158:1–6, Society for Endocrinology (Jul. 1998).

Lee, M.M. et al., "Mullerian Inhibiting Substance in Humans: Normal Levels from Infancy to Adulthood," *J. Clin. Endocrinol. Metabol.* 81:571–576, The Endocrine Society (1996).

Lee, M.M. et al., "Müllerian–Inhibiting Substance Type II Receptor Expression and Function in Purified Rat Leydig Cells," *Endocrinology* 140:2819–2827, The Endocrine Society (Jun. 1999).

Lyet, L. et al., "Ontogeny of Reproductive Abnormalities Induced by Deregulation of Anti–Müllerian Hormone Expression in Transgenic Mice," *Biol. Reproduct.* 52:444–454, Society for the Study of Reproduction (1995).

MacLaughlin, D.T. et al., "Bioassay, Purification, Cloning, and Expression of Müllerian Inhibiting Substance," *Methods Enzymol.* 198:358–369, Academic Press, Inc. (1991).

MacLaughlin, D.T. et al., "Mullerian Duct Regression and Antiproliferative Bioactivities of Mullerian Inhibiting Substance Reside in its Carboxy–Terminal Domain," *Endocrinology* 131:291–296, The Endocrine Society (1992).

Mishina, Y. et al., "Genetic analysis of the Müllerian–inhibiting substance signal transduction pathway in mammalian sexual differentiation," *Genes Develop.* 10:2577–2587, Cold Spring Laboratory Press (1996).

O'Shaughnessy, P.J. et al., "Fetal Development of Leydig Cell Activity in the Mouse Is Independent of Pituitary Gonadotroph Function," *Endocrinology* 139:1141–1146, The Endocrine Society (Mar. 1998).

Parry, R.L. et al., "Recombinant Human Mullerian Inhibiting Substance Inhibits Human Ocular Melanoma Cell Lines in Vivo and in Vitro," *Cancer Res.* 52:1182–1186, American Association for Cancer Research (1992).

Pepinsky, R.B. et al., "Proteolytic Processing of Mullerian Inhibiting Substance Produces a Transforming Growth Factor–β–like Fragment," *J. Biol. Chem.* 263:18961–18964, The American Society for Biochemistry and Molecular Biology, Inc. (1988).

Picard, J.–Y. et al., "Cloning and expression of cDNA for anti–Müllerian hormone," *Proc. Natl. Acad. Sci. USA* 83:5464–5468, National Academy of Sciences (1986).

Racine, C. et al., "Receptors for anti–Müllerian hormone on Leydig cells are responsible for its effects on steroidogenesis and cell differentiation," *Proc. Natl. Acad. Sci. USA* 95:594–599, National Academy of Sciences (Jan. 1998).

Ragin, R.C. et al., "Human Müllerian Inhibiting Substance: Enhanced Purification Imparts Biochemical Stability and Restores Antiproliferative Effects," *Protein Expression and Purification* 3:236–245, Academic Press, Inc. (1992).

Rey, R. et al., "Anti–Müllerian Hormone and Testosterone Serum Levels Are Inversely Related during Normal and Precocious Pubertal Development," *J. Clin. Endocrinol. Metabol.* 77:1220–1226, The Endocrine Society (1993).

Rouiller–Fabre, V. et al., "Effect of Anti–Mullerian Hormone on Sertoli and Leydig Cell Functions in Fetal and Immature Rats," *Endocrinology* 139:1213–1220, The Endocrine Society (Mar. 1998).

Saez, J.M., "Leydig Cells: Endocrine, Paracrine, and Autocrine Regulation," *Endcrine Rev.* 15:574–626, The Endocrine Society (1994).

Segev, D.L. et al., "Müllerian Inhibiting Substance Inhibits Breast Cancer Cel Growth through and NFγB–mediated Pathway," *J. Biol. Chem.* 275:28371–28379, The American Society for Biochemistry and Molecular Biology, Inc. (Jun. 2000).

Seifer, D.B. et al., "Gonadotropin–Releasing Hormone Agonist–Induced Differences in Granulosa Cell Cycle Kinetics Are Associated with Alterations in Follicular Fluid Mullerian–Inhibiting Substance and Androgen Content," *J. Clin. Endocrinol. Metabol.* 76:711–714, The Endocrine Society (1993).

Shah, P.C. et al., "Müllerian Inhibiting Substance as a Model for the Transforming Growth Factorβ Family: Development of New Treatment Strategies," *Sem. Pediat. Surg.* 5:182–190, W.B. Saunders Company (1996).

Swain, A. et al., "Dax1 antagonizes Sry action in mammalian sex determination," *Nature* 391:761–767, Macmillan Publishers (Feb. 1998).

Takahashi, M. et al., "Müllerian inhibiting substance as oocyte meiosis inhibitor," *Mol. Cell. Endocrinol.* 47:225–234, Elsevier Scientific Publishers Ireland, Ltd. (1986).

Teixeira et al., "Molecular Characterization of the MIS Type II Receptor," application for National Institute of Child Health and Human Development grant No. 1 F32 HD07954–01 (Mar. 1, 1995 or later).

Teixeira, J. and Donahoe, P.K., "Molecular Biology of MIS and Its Receptors," *J. Androl.* 17:36–341, American Society for Andrology (1996).

Teixeira, J. et al., "Developmental Expression of a Candidate Müllerian Inhibiting Substance Type II Receptor," *Endocrinology* 137:160–165, The Endocrine Society (1996).

Teixeria, J.M. et al., "Regulation of MIS Type II Receptor And Target Genes," application for National Cancer Institute grant No. 1 R29 CA79459–01 (Apr. 1, 1998 or later).

Teixeira, J. et al., "Müllerian–Inhibiting Substance Regulates Androgen Synthesis at the Transcriptional Level," *Endocrinology* 140:4732–4738, The Endocrine Society (Sep. 14, 1999).

Tsafriri, A. et al., "Immunopurified Anti–Müllerian Hormone Does Not Inhibit Spontaneous Resumption of Meiosis In Vitro of Rat Oocytes," *Biol. Reproduct.* 38:481–485, The Society for the Study of Reproduction (1988).

Ueno, S. et al., "Human Recombinant Mullerian Inhibiting Substance Inhibition of Rat Oocyte Meiosis Is Reversed by Epidermal Growth Factor in Vitro," *Endocrinology* 123:1652–1659, The Endocrine Society (1988).

Wallen, J.W. et al., "Minimal Antiproliferative Effect of Recombinant Mullerian Inhibiting Substance on Gynecological Tumor Cell Lines and Tumor Explants," *Cancer Res.* 49:2005–2011, American Association for Cancer Research (1989).

Wilson, C.A. et al., "Mullerian Inhibiting Substance Requires Its N–Terminal Domain for Maintenance of Biology Activity, a Novel Finding within the Transforming Growth Factor–β Superfamily," *Mol. Endocrinol.* 7:247–257, The Endocrine Society (1993).

\* cited by examiner

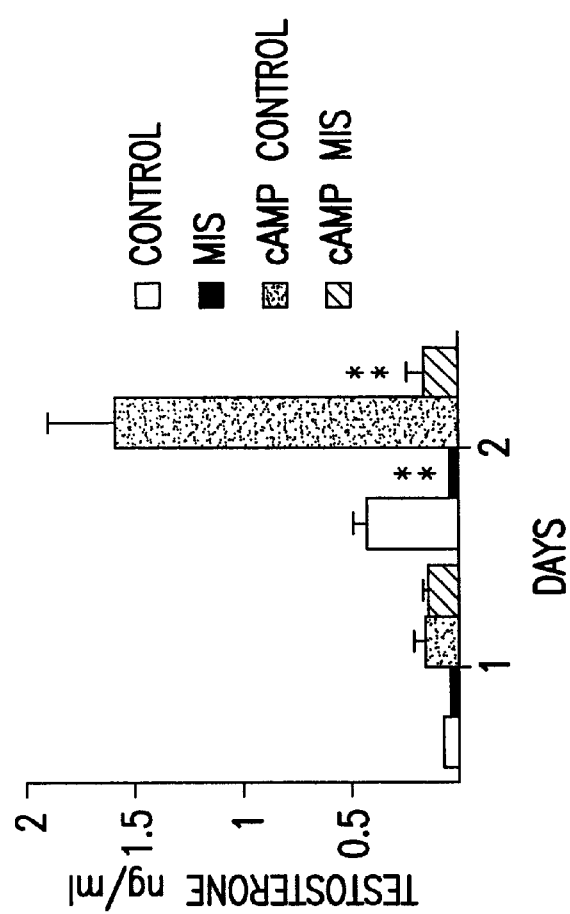
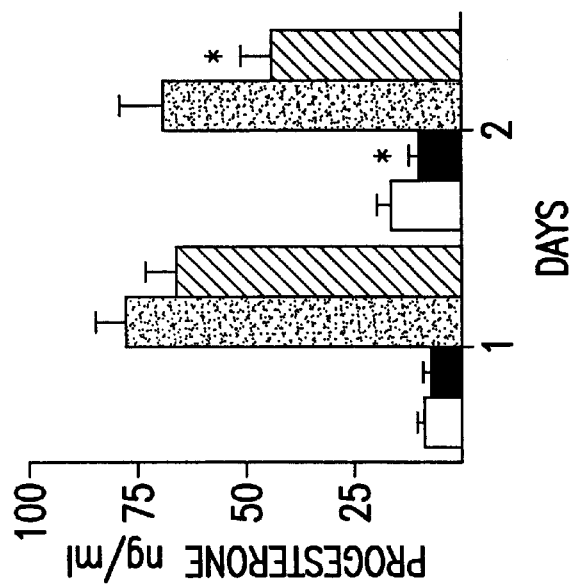
FIG. 3A
FIG. 3B

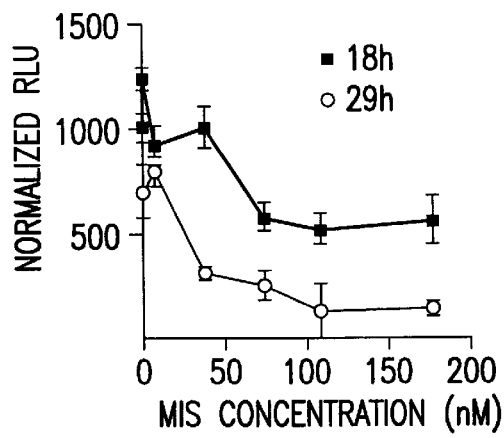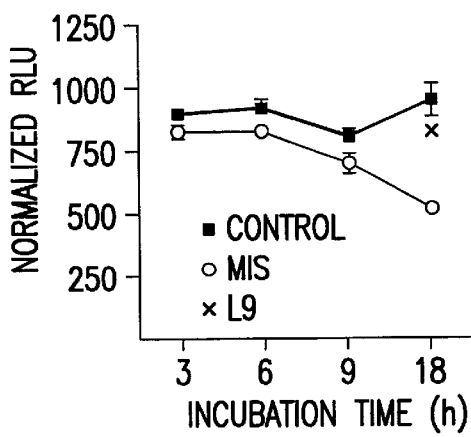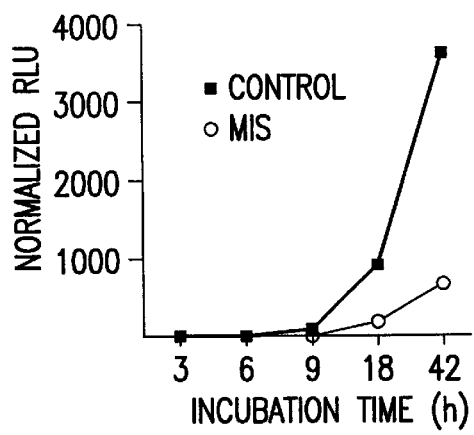
FIG.5A
FIG.5B
FIG.5C

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 1
gagctcgagt attggcattg cgtccc                                        26

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 2
ctcgagggca gatggccagc tgtgga                                        26

USE OF MULLERIAN INHIBITING SUBSTANCE FOR TREATING EXCESS ANDROGEN STATES

This application claims priority benefit of U.S. provisional application No. 60/153,674, filed Sep. 14, 1999, and U.S. provisional application No. 60/153,940, filed Sep. 15, 1999, which are hereby incorporated by reference.

STATEMENTS AS TO INVENTIONS MADE UNDER FEDERALLY-SPONSORED RESEARCH AND DEVELOPMENT

Part of the work performed during development of this invention utilized U.S. Government funds from National Cancer Institute grant no. R29CA79459, and from National Institute of Child Health and Human Development grant nos. RO1-HD-32112, P30-HD-28138, F32-HD-07954, and U54HD31398. The U.S. Government has certain rights in this invention.

BACKGROUND OF THE INVENTION

1. Field of the Invention

This application is directed generally to methods of treating prostate cancer, polycystic ovarian disease, benign prostatic hypertrophy, and precocious puberty.

2. Related Art

Mullerian inhibiting substance (MIS) is a member of the transforming growth factor-β (TGFβ) family of growth and differentiation factors. After the sexually indifferent gonad commits to testis development under the influence of the testis-determining factor, SRY, Sertoli cells of the fetal testis begin procuring MIS, which is a phenotypic hallmark of testis development (Swain et al., *Nature* 391:761–767 (1998)). MIS, also known as anti-Mullerian hormone (Jossa et al., *Recent Prog. Horm. Res.* 48: 1–59 (1993)), is absolutely required for normal male reproductive tract development because it affects the regression of the Mullerian duct of the bipotential urogenital ridge, which, is left undisturbed, would give rise to female reproductive tract structures such as the uterus, Fallopian tubes, and upper vagina (Jost, A., *Arch. Anal. Microsc. Morphol. Exp.* 36:271–315 (1947); Cate et al., *Cell* 45:685–698 (1986); Teixeira and Donohoe, *J. Androl.* 17:336–341 (1996)). Adult ovaries and testes also produce MIS, albeit at much lower levels than in fetal males, and the functional roles played by MIS in these settings have not been fully elucidated (Ueno et al., *Endocrinology* 123:1652–1659 (1988); Tsafriri et al., *Biol. Reprod.* 38:481–485 (1988)). However, studies in the rat suggest a role for MIS in oocyte maturation (Takahashi et al., *Mol. Cell Endocrinol.* 47:225–234 (1986)) and in human ovary in blocking granulosa cell proliferation and reducing steroidogenesis (Kim et al., *J. Clin. Endocrinol. Metab.* 75:911–917 (1992), Seifer et al., *J. Clin. Endocrinol. Metab.* 76:711–714 (1993)).

SUMMARY OF THE INVENTION

The present invention provides a method of treating a condition or disease characterized by an excess of one or more androgens, the method comprising administering an effective amount of MIS to a patient.

The present invention also provides a method of treating a condition or disease characterized by an excess of one or more androgens, the method comprising administering an effective amount of a nucleic acid encoding MIS to a patient.

The present invention also provides a method of decreasing the plasma level of one or more androgens, the method comprising administering to a patient an effective amount of MIS, wherein the amount of MIS is sufficient to decrease the plasma level of the one or more androgens below the normal level for the one or more androgens.

The present invention also provides a method of decreasing the plasma level of one or more androgens, the method comprising administering to a patient an effective amount of nucleic acid encoding MIS, wherein the amount of MIS is sufficient to decrease the plasma level of the one or more androgens below the normal level for the one or more androgens.

The methods of the present invention are particularly well-suited for the treatment of prostate cancer, polycystic ovarian disease, benign prostatic hypertrophy, and precocious puberty.

BRIEF DESCRIPTION OF THE FIGURES

FIGS. 3A and 3B depict the results of an analysis of steroid production in MA-10 cells. Culture medium was collected and assayed by RLA for total accumulated progesterone (FIG. 3A) and testosterone (FIG. 3B); shown are levels after 1 or 2 days of treatment with 105 nM MIS in presence or absence of 50 μM cAMP. Cross morphology was indistinguishable between MIS-treated and untreated cells. There was no significant difference between total protein content in MIS-treated and untreated cells as measured previously (Bradford, M. M., *Anal Biochem.* 72:248–254 (1976)). Error bars represent the SEM. *, $P<0.05$; , $P<0.001$; *, $P<0.0001$. Significance was measured using Student's t test.

In FIG. 4A, R2C cells were treated for 3 h with MIS (105 nM) or vehicle control as indicated. Total RNA was extracted from the cell cultures after incubation, and Northern blots were performed using 10 μg of each sample, with 30-day postnatal rat testis RNA as a control. In FIG. 4B, MA-10 cells were treated for 18 h with MIS (105 nM) or vehicle control in the presence or absence of $(Bu)_2$-cAMP (50 μM) as indicated. In FIG. 4C, MA-10 cells were treated with 10 μM/ml cyclohexamide 30 min. before treatment with MIS or vehicle control, as indicated.

FIGS. 5A–C depict the results of a study of MIS regulation of the P450c17α promoter. A promoter/reported minigene system employing the luciferase reporter gene was used to characterize the promoter of the P450c17α gene. In FIG. 5A, MA-10 cells were incubated, 24 h post-transfection, with vehicle control or 1.4, 7, 35, 70, 105 and 175 nM MIS for 18 or 29 h. Cell extracts were assayed for firefly luciferase and renilla luciferase activity, and the results are shown as firefly/renilla values normalized to vehicle control values at 1000 relative light units. In FIG. 5B, Cells were incubated with vehicle control or 105 nM MIS for the indicated periods of time starting 24 h after transfection. Cells were also incubated with an inactive L9 noncleavable mutant MIS for 18 h (shown with an asterisk). Cell extracts were assayed for luciferase activity, and the results are shown as firefly/renilla values normalized to the 18 h vehicle control values at 1000 relative light units. In FIG. 5C, Cells were treated with 105 nM MIS at the start of transfection and incubated for the indicated periods of time. Cell extracts were assayed for luciferase activity, and the results are shown as firefly/renilla values normalized to 18 h vehicle control values at 1000 relative light units. Error bars represent the SEM.

DETAILED DESCRIPTION

Figure 1:
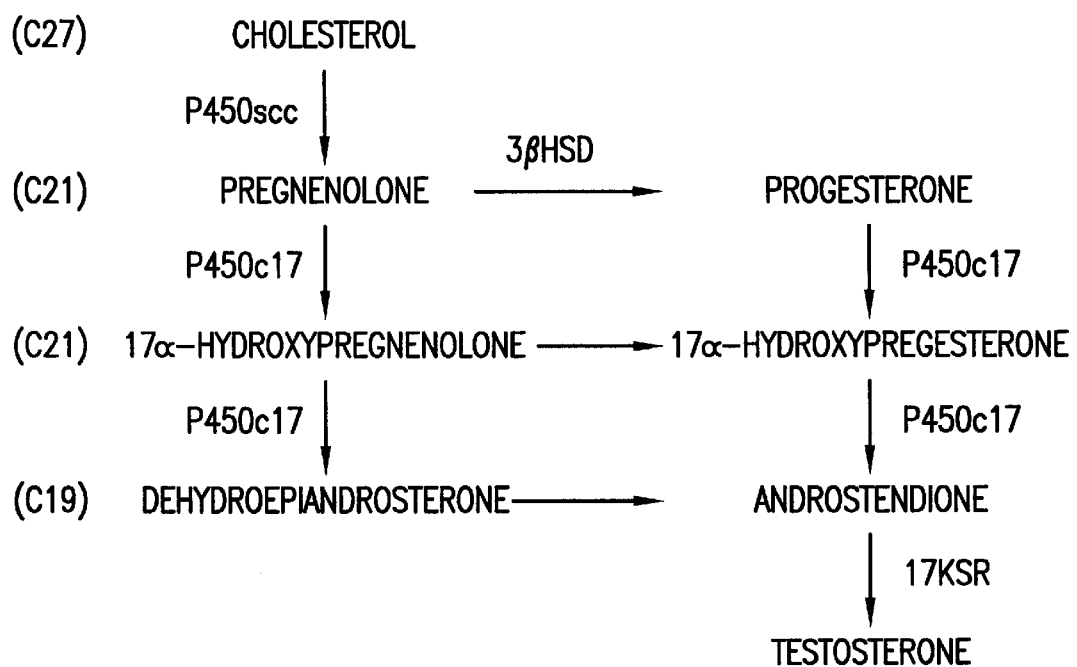
FIG. 1 depicts the pathways of testosterone biosynthesis. 21-Carbon testosterone is synthesized from the 27-carbon cholesterol molecule by the activities of P450-scc (cytochrome P450 side-chain cleavage), P450c17 (cytochrome P450c17 hydroxylase/lyase), 3βHSD, and 17KSR (17-ketosteroid reductase).

The terms "mullerian inhibiting substance," "MIS," and anti-Mullerian hormone" are synonymous.

Conditions or diseases characterized by an excess of one or more androgens include, but are not limited to, a condition or disease selected from the group consisting of polycystic ovarian disease or syndrome, precocious puberty, and McCune-Albright syndrome. Whether androgen levels are excessive can be readily diagnosed by one of ordinary skill in the art, using clinical chemisty, including urinalysis, and blood, serum, or plasma analysis.

The term "androgen" includes testosterone and its metabolites, such as dihydrotestosterone, androsterone, estradiol, and etiocholanolone. Thus, a condition or disease characterized by an excess of one or more androgens, such as testosterone or one of its metabolites, is increased, relative to the normal level of the androgen. For example, the normal plasma level of testosterone is about 10–35 nmol/L (about 3–10 ng/mL). See *Harrison's Principles of Internal Medicine,* 14th Edition, Fauci, A. S. et al., Eds., McGaw-Hill, New York (1998), at page 2040, Table 332-2, the content of which is incorporated by reference.

Whether a patient has a condition or disease characterized by an excess of one or more androgens, and particularly polycystic ovarian disease or syndrome or precocious puberty, can be readily diagnosed by one of ordinary skill in the art, based upon physical examination, clinical chemistry analysis, family history, and patient interviews. See *Harrison's Principles of Internal Medicine,* 14th Edition, Fauci, A. S. et al., Eds., McGaw-Hill, New York (1998).

In patients with benign prostatic hypertrophy, to whom MIS, or nucleic acid encoding MIS, is administered, the extent of prostatic hypertrophy is diminished or decreased. The extent of prostatic hypertrophy, and changes therein, can be readily determined by one of ordinary skill in the art.

In patients with prostatic cancer, to whom MIS, or nucleic acid encoding MIS, is administered, the progression of the tumor, whether primary or metastatic, is halted or slowed. The progression of a tumor, whether primary or metastatic, can be readily determined by one of ordinary skill in the art, such as by tissue biopsy, ultrasound, magnetic resonance imaging (MRI), computer aided tomography (CAT scan), or palpation.

Müllerian Inhibiting Substance (MIS) is produced by the fetal testis as a 140 kDa glycosylated disulfide-linked homodimer that causes regression of the Müllerian duct in the male fetus. Under reducing conditions, the protein migrates on gel electrophoresis at an apparent molecular weight of 70 kDa. The protein can be proteolytically cleaved by exogenous plasmin into two distinct fragments that migrate electrophoretically as 57 kDa and 12.5 kDa moieties with cleavage at residue 427 of the intact 535 amino acid monomer (Pepinsky, et al., *J. Biol. Chem.* 263:18961-4 (1988)).

The term "carboxy-terminal (C-terminal) fragment of MIS" is intended to include compounds and materials structurally similar to the about 12.5 kDa (about 25 kDa under non-reducing conditions) C-terminal fragment of MIS resulting from proteolytic (e.g., plasmin) cleavage at residue 427 of the intact 535 amino acid human MIS monomer. The proteolytic (e.g., plasmin) cleavage site is at residue 443 of the 551 amino acid bovine MIS molecule. In particular, "carboxy-terminal (C-terminal) fragment of MIS" is intended to include the about 25 kDa homodimeric C-terminal fragment of MIS.

By "N-terminal fragment of MIS" is intended the about 57 kDa fragment resulting from the above-noted cleavage at residue 427 of the intact 535 amino acid human MIS monomer (residue 443 of the 551 amino acid bovine MIS).

The complete sequence nucleotide sequence for MIS is disclosed in U.S. Pat. No. 5,047,336, which is hereby incorporated by reference. The C-terminal amino acid and nucleotide sequences for bovine MIS are shown in FIG. 17 of U.S. Pat. No. 5,661,126, which is hereby incorporated by reference in its entirety. The C-terminal amino acid and nucleotide sequences for human MIS are shown in FIG. 18 of U.S. Pat. No. 5,661,126. A comparison of the amino acid sequence for human and bovine MIS, showing the - and C-terminal domains is shown in Cate et al., *Handbook of Fxperimental Pharmacology* 95/II:184, edited by M. B. Sporn and A. B. Roberts, Spinger-Verlag Berlin Heidelberg (1990), which are hereby incorporated by reference.

Additionally, the methods of the present invention can be practiced using mutant forms of the C-terminal fragment of MIS which have substantially the same biological activity as the C-terminal fragment of MIS. Examples of such mutant forms would be C-terminal fragment of MIS molecules carrying a deletion, insertion, or alteration of amino acid sequence. In particular, the C-terminal fragment of MIS can be modified to increase its half-life in vivo. For example, addition of one or more amino acids or other chemical agents to the amino and/or carboxyl end of the C-terminal fragment can be used to increase the fragment's stability.

The C-terminal fragment of MIS can be obtained from a mammalian source or through the use of recombinant DNA technology, or from chemical synthesis of the C-terminal polypeptide.

A gene is said to be a "recombinant" gene if it results from the application of Recombinant DNA Techniques. Examples of recombinant DNA techniques include cloning, mutagenesis, transformation, etc. Recombinant DNA Techniques are disclosed in Maniatis et al., *Molecular Cloning: A Laboratory Manual,* Cold Spring Harbor, N.Y. (1982, 1989). "Recombinant MIS" refers to MIS polypeptide, or a fragment thereof, and particularly the C-terminal fragment, that is prepared using recombinant means.

Recombinant MIS can be expressed in a protein expression system. The use of prokaryotic and eukaryotic expression systems is well understood by those of ordinary skill in the art. For example, bacterial (e.g., *E. coli*), fungi (e.g., yeast), mammalian cells (e.g., CHO cells, COS cells) or insect cells (e.g., baculovirus cells) expression systems can be used. For example, the C-terminal fragment (human or bovine) can be readily produced by the recombinant DNA techniques described in U.S. Pat. No. 5,047,336, which is fully incorporated by reference herein. Of particular interest is expression of the C-terminal fragment in *E. coli* and other bacteria, since the C-terminal fragment is not glycosylated.

Within a specific cloning or expression vehicle, various sites may be selected for insertion of the gene coding for MIS or C-terminal fragment of MIS. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of recombinant DNA sequences. These expression control sequences include, for example, the lac system, the β-lactamase system, the trp system, the tac system, the trc system, the major operator and promoter regions of phase λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of recombinant DNA sequences, these DNA sequences are operatively-linked to one or more of the above-described expression control sequences in the expression vector. Such operative linking, which may be effected before or after the MIS or C-terminal fragment of MIS DNA sequence is inserted into a cloning vehicle, enables the expression control sequences to control and promote the expression of the DNA sequence.

The vector or expression vehicle, and in particular the sites chosen therein for insertion of the selected DNA fragment and the expression control sequence employed in this invention, is determined by a variety of factors, e.g., number of sites susceptible to a particular restriction enzyme, size of the protein to be expressed, expression characteristics such as start and stop codons relative to the vector sequences, and other factors recognized by those of skill in the art. The choice of a vector, expression control sequence, and insertion site for the MIS or C-terminal fragment of MIS DNA sequence is determined by a balance of these factors, not all selections being equally effective for a given case.

It should also be understood that the DNA sequences coding for MIS or the C-terminal fragment of MIS that are inserted at the selected site of a cloning or expression vehicle may include nucleotides which are not part of the actual gene coding for MIS or the C-terminal fragment of MIS or may include only a fragment of the actual gene. It is only required that whatever DNA sequence is employed, a transformed host will produce MIS or the C-terminal fragment of MIS. For example, the MIS DNA sequences of this invention may be fused in the same reading frame in an expression vector of this invention to at least a portion of a DNA sequence coding for at least one eukaryotic or prokaryotic signal sequence, or combinations thereof. Such constructions enable the production of, for example, a methionyl or other peptidyl-MIS polypeptide, that is part of this invention. This N-terminal methionine or peptide may either then be cleaved intra- or extra-cellularly by a variety of known processes or the MIS polypeptide with the methionine or peptide attached may be used, uncleaved, in the pharmaceutical compositions and methods of this invention.

The cloning vehicle or expression vector containing the MIS or C-terminal fragment of MIS polypeptide coding sequences of this invention is employed in accordance with this invention to transform tumor cells so as to permit expression of an effective amount of MIS or an effective amount of the C-terminal fragment of MIS to inhibit primary or metastatic tumor growth.

As indicated, it should be understood that the MIS polypeptide (prepared in accordance with this invention) may include polypeptides in the form of fused proteins (e.g., linked to prokaryotic, eukaryotic or combination N-terminal segment to direct excretion, improve stability, improve purification or improve possible cleavage at amino acid residue 443 to release an active C-terminal fragment), in the form of a precursor of MIS (e.g., starting with all or parts of a MIS signal sequence of other eukaryotic or prokaryotic signal sequences), in the form of a mature MIS polypeptide, or in the form of an fmet-MIS polypeptide.

The present invention also encompasses substituting codons for those of the MIS or C-terminal fragment of MIS nucleotide sequences. These substituted codons may code for amino acids identical to those coded for by the codons replaced but result in higher yield of the polypeptide. Alternatively, the replacement of one or a combination of codons leading to amino acid replacement or to a longer or shorter polypeptide may alter its properties in a useful way (e.g., increase the stability, increase the solubility or increase the therapeutic activity).

Alternatively, non-recombinant MIS or a fragment thereof, and particularly the C-terminal fragment, can be used in the methods of the present invention. Methods for purifying non-recombinant MIS are well-known to those of ordinary skill in the art. See U.S. Pat. Nos. 4,404,188, 4,487,833 and 5,011,687.

MIS Polypeptide Delivery Methods

MIS polypeptide, or a fragment thereof, and MIS-encoding nucleic acid can be administered in the form of a pharmaceutical compositions. The pharmaceutical composition can be formulated according to known methods to prepare pharmaceutically useful compositions, whereby MIS or the C-terminal fragment of MIS or their functional derivatives are combined in admixture with a pharmaceutically acceptable carrier vehicle. Suitable vehicles and their formulation, inclusive of other human proteins, i.e., human serum albumin, are described for example in *Remington's Pharmaceutical Sciences,* 8th edition, A. R. Gennaro, Ed., Mack Publ., Easton, Pa. (1990). In order to from a pharmaceutically acceptable composition suitable for effective administration, such compositions will contain an effective amount of MIS or the C-terminal fragment of MIS, or their functional derivatives, together with a suitable amount of carrier vehicle.

In one embodiment of the present invention, an "effective amount" of MIS is one which is sufficient to inhibit the progression of and/or reduce the severity of polycystic ovarian disease or syndrome, or to slow and/or halt the progression of precocious puberty. Likewise, an "effective amount" of the C-terminal fragment of MIS is one which is sufficient to inhibit the progression of and/or reduce the severity of polycystic ovarian disease or syndrome, or to slow and/or halt the progression of precocious puberty.

In another embodiment of the present invention, an "effective amount" of MIS is one which is sufficient to decrease the plasma level of one or more androgens, including testosterone and/or its metabolites, such as dihydrotestosterone, androsterone, estradiol, and etiocholanolone, below the normal level. The normal plasma level of testosterone below about 10–35 nmol/L (about 3–10 ng/mL). See *Harrison's Principles of Internal Medicine*, 14$^{th}$ Edition, Fauci, A. S. et al., Eds., McGaw-Hill, New York (1998), at page 2040, Table 332-2, the content of which is incorporated by reference. In a preferred embodiment, an effective amount of MIS is one which is sufficient to decrease the plasma level of testosterone below about 10–35 nmol/L (about 3–10 ng/mL). In a particularly preferred embodiment, an effective amount of MIS is one which is sufficient to decrease the plasma level of testosterone below about 15–30 nmol/L. In a still more preferred embodiment, an effective amount of MIS is one which is sufficient to decrease the plasma level of testosterone below about 20–25 nmol/L.

The effective amount may vary depending upon criteria such as the age, weight, physical condition, past medical history, and sensitivity of the recipient. The effective amount will also vary depending on whether administration is oral, intravenous, intramuscular, subcutaneous, local, or by direct application to the tumor. In the case of direct tumor application, it is preferable that a final serum concentration of at least 0.1 nM, preferably about 0.1–1.0 nM, of MIS be achieved. Likewise, for direct tumor application of the C-terminal fragment of MIS, it is preferable that a final serum concentration of at least 0.1 nM, preferably about 0.1–1.0 nM, of the C-terminal fragment of MIS be achieved. Effective individual dosage through the additionally named means of administration can be readily determined by methods well known to those of ordinary skill in the art. For example, using the size ratio calculation as detailed above, one of ordinary skill in the art can determine optimal dosage levels for any means of administration. In treating a patient, it is preferable to achieve a serum level of at least 10 ng/ml of MIS. In treating a patient with the C-terminal fragment of MIS, it is preferable to achieve a serum level ranging from about 1 ng/ml to about 20 µg/ml of the C-terminal fragment of MIS.

A composition is said to be "pharmacologically acceptable" if its administration can be tolerated by a recipient patient. Such an agent is said to be physiologically significant if its presence results in a detectable change in the physiology of a recipient patient.

Compositions containing MIS or the C-terminal fragment of MIS or their functional derivatives may be administered orally, intravenously, intramuscularly, subcutaneously, or locally. Additional pharmaceutical methods may be employed to control the duration of action. Controlled release preparations may be achieved by the use of polymers to complex or adsorb MIS or the C-terminal fragment of MIS or their functional derivatives. The controlled delivery may be exercised by selecting appropriate macromolecules (for example polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release.

Another possible method to control the duration of action by controlled release preparations is to incorporate MIS or the C-terminal fragment of MIS into particles of a polymeric material such as polyesters, polyamino acids, hydrogels, poly(lactic acid) or ethylene vinyl acetate copolymers. Alternatively, instead of incorporating MIS or the C-terminal fragment of MIS into these polymeric particles, it is possible to entrap MIS or the C-terminal fragment of MIS in microcapsules prepared, for example, by coacervation techniques or by interfacial polymerization, for example, hydroxymethylcellulose or gelatin microcapsules and poly(methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences*, 18th edition, A. R. Gennaro, Ed., Mack Publ., Easton, Pa. (1990).

A "functional derivative" of MIS is a compound which possesses a biological activity (either functional or structural) that is substantially similar to a biological activity of MIS. The term "functional derivatives" is intended to include the "fragments," "variants," "analogs," or "chemical derivatives" of a molecule. A "fragment" of a molecule such as either MIS, is meant to refer to any polypeptide subset of the molecule. Fragments of MIS which has activity and which are soluble (i.e not membrane bound) are especially preferred. A "variant" of a molecule such MIS is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a molecule such as MIS is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences*, 18th edition, A. R. Gennaro, Ed., Mack Publ., Easton, Pa. (1990). "Toxin-derivatized" molecules constitute a special class of "chemical derivatives." A "toxin-derivatized" molecule is a molecule (such as MIS or an antibody to its receptor) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

MIS (or its functional derivatives, agonists, or antagonists) may be administered to patients intravenously, intramuscularly, subcutaneously, enterally, or parenterally. When administering such compounds by injection, the administration may be by continuous infusion, or by single or multiple boluses.

MIS molecules (and their functional derivatives, agonists and antagonists can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences*, 18th edition, A. R. Gennaro, Ed., Mack Publ., Easton, Pa. (1990). In order to form a pharmaceutically acceptable composition suitable for effective administration, such compositions will contain an effective amount of MIS molecule, or its functional derivatives, agonists, or antagonists, together with a suitable amount of carrier vehicle.

Additional pharmaceutical methods may be employed to control the duration of action. Control release preparations may be achieved through the use of polymers to complex or absorb MIS or its functional derivatives, agonists, or antagonists. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the MIS molecule, or its functional derivatives, agonists, or antagonists, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences*, 18th edition, A. R. Gennaro, Ed., Mack Publ., Easton, Pa. (1990). The compositions of the present invention may be prepared as articles of manufacture, such as "kits." Preferably, such kits will contain two or more containers which are specially adapted to receive MIS or one of its functional derivatives, and an agonist of MIS.

The term "patient" is intended to include animal patients. More preferably, "patient" is intended to include mammalian patients, most preferably, human patients.

The term "protein fragment" is meant to include both synthetic and naturally-occurring amino acid sequences derivable from the naturally occurring amino acid sequence of MIS. The protein is said to be "derivable from the naturally-occurring amino acid sequence of MIS" if it can be obtained by fragmenting the naturally-occurring chosen sequence of MIS, or if it can be synthesized based upon a knowledge of the sequence of the naturally occurring amino acid sequence or of the genetic material (DNA or RNA) which encodes this sequence.

MIS Gene Therapy Methods

In one embodiment of the present invention, an "effective amount" of nucleic acid encoding MIS is one which is sufficient to inhibit the progression of and/or reduce the severity of polycystic ovarian disease or syndrome, or to slow and/or halt the progression of precocious puberty. Likewise, an "effective amount" of nucleic acid encoding the C-terminal fragment of MIS is one which is sufficient to inhibit the progression of and/or reduce the severity of polycystic ovarian disease or syndrome, or to slow and/or halt the progression of precocious puberty.

In another embodiment of the present invention, an "effective amount" of nucleic acid encoding MIS is one which is sufficient to decrease the plasma level of one or more androgens, including testosterone and/or its metabolites, such as dihydrotestosterone, androsterone, estradiol, and etiocholanolone, below the normal level. The normal plasma level of testosterone below about 10–35 nmol/L (about 3–10 ng/mL). See *Harrison's Principles of Internal Medicine*, 14$^{th}$ Edition, Fauci, A. S. et al., Eds., McGaw-Hill, New York (1998), at page 2040, Table 332-2, the content of which is incorporated by reference. In a preferred embodiment, an effective amount of MIS is one which is sufficient to decrease the plasma level of testosterone below about 10–35 nmol/L (about 3–10 ng/mL). In a particularly preferred embodiment, an effective amount of MIS is one which is sufficient to decrease the plasma level of testosterone below about 15–30 nmol/L. In a still more preferred embodiment, an effective amount of MIS is one which is sufficient to decrease the plasma level of testosterone below about 20–25 nmol/L.

Whether a vector contains a gene capable of expressing an "effective amount of MIS" or an "effective amount of the C-terminal fragment of MIS" can be determined following the protocols set forth in Example 4 in U.S. Pat. No. 5,661,126, which is hereby incorporated by reference in its entirety.

The gene therapy methods relate to the introduction of nucleic acid (DNA, RNA and antisense DNA or RNA) sequences into an animal to achieve expression of the MIS polypeptide of the present invention. This method requires a polynucleotide which codes for an MIS polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to an MIS polynucleotide ex vivo, with the engineered cells then being provided to a patient to be treated with the polypeptide. Such methods are well-known in the art. For example, see Beildegrun, A., et al., *J. Natl. Cancer Inst.* 85:207–216 (1993); Ferrantini, M. et al., *Cancer Research* 53:1107–1112 (1993), Ferrantini, M. et al., *J. Immunology* 153: 4604–4615 (1994); Kaido, T., et al., *Int. J. Cancer* 60: 221–229 (1995); Ogura, H., et al., *Cancer Research* 50: 5102–5106 (1990); Santodonato, L., et al., *Human Gene Therapy* 7:1–10 (1996); Santodonato, L., et al., Gene Therapy 4:1246–1255 (1997); and Zhang, J. -F. et al., *Cancer Gene Therapy* 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the MIS polynucleotide constructs can be delivered by any method that delivers injectable materials to the cells of an animal, such as, injection into the interstitial space of tissues (heart, muscle, skin, lung, liver, and the like). The MIS polynucleotide constructs may be delivered in a pharmaceutically acceptable liquid or aqueous carrier.

In one embodiment, the MIS polynucleotide is delivered free of any delivery vehicle that acts to assist, promote or facilitate entry into the cell. In another embodiment, the MIS polynucleotide is delivered free of viral sequences. In another embodiment, the MIS polynucleotide is delivered free of viral particles. In another embodiment, the MIS polynucleotide is delivered free of liposome formulations. In another embodiment, the MIS polynucleotide is delivered free of lipofectin. In another embodiment, the MIS polynucleotide is delivered free of precipitating agents. However, the MIS polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The MIS polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of MIS DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs, the b-actin promoter; and human growth hormone promoters. The promoter also may be the native promoter for MIS.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The MIS polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked MIS DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the MIS polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl Acad. Sci. USA* (1987) 84:7413–7416, which is herein incorporated by reference); mRNA (Malone et al., *Proc. Natl. Acad. Sci. USA* (1989) 86:6077–6081, which is herein incorporated by reference); and purified transcription factors (Debs et al., *J. Biol. Chem.* (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl. Acad. Sci. USA* (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P.

Felgner et al., *Proc. Natl. Acad. Sci. USA* 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology* (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* (1975) 394:483; Wilson et al., *Cell* (1979) 17:77); ether injection (Deamer, D. and Bangham, A., *Biochim. Biophys. Acta* (1976) 443:629, Ostro et al., *Biochem. Biophys. Res. Commun.* (1977) 76:836; Fraley et al., *Proc. Natl. Acad. Sci. USA* (1979) 76:3348); detergent dialysis (Enoch, H. and Strittmatter, P., *Proc. Natl. Acad. Sci. USA* (1979)76:145); and reverse-phase evaporation (REV) (Fraley et al., *J. Biol. Chem.* (1 980) 255:10431; Szoka, F. and Papahadjopoulos, D., *Proc. Natl. Acad. Sci. USA* (1978) 75:145; Schaefer-Ridder et al., *Science* (1982) 215:166), which are herein incorporated by reference.

Generally, the ratio of DNA to liposomes will be from about 10:1 to about 1:10. Preferably, the ration will be from about 5:1 to about 1:5. More preferably, the ratio will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/29469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/29469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding MIS. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA 12, T19-14X, VT-19-17-H2, RCRE, RCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding MIS. Such retroviral vector particles then may be employed, to transduce eukaryotic cells, either in vitro or in vivo. The transduced eukaryotic cells will express MIS.

In certain other embodiments, cells are engineered, ex vivo or in vivo, with MIS polynucleotide contained in an adenovirus vector. Adenovirus can be manipulated such that it encodes and expresses MIS, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252:431–434; Rosenfeld et al., (1992) *Cell* 68:143–155). Furthermore, extensive studies to attempt to establish adenovirus as a causative agent in human cancer were uniformly negative (Green, M. et al. (1979) *Proc. Natl. Acad Sci. USA* 76:6606).

Suitable adenoviral vectors useful in the present invention are described, for example, in Kozarsky and Wilson, *Curr.*

Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The MIS polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the MIS polynucleotide construct. These viral particles are then used to transduce eukaryotic cells, either ex vivo or in vivo. The transduced cells will contain the MIS polynucleotide construct integrated into its genome, and will express MIS.

Another method of gene therapy involves operably associating heterologous control regions and endogenous polynucleotide sequences (e.g. encoding MIS) via homologous recombination (see, e.g., U.S. Pat. No. 5,641,670, issued Jun. 24, 1997; International Publication No. WO 96/29411, published Sept. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the MIS desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous MIS sequence is placed under the control of the promoter. The promoter then drives the expression of the endogenous MIS sequence.

Preferably, the polynucleotide encoding MIS contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician.

Phenotypes of genetically altered adult mice have yielded several clues for possible role for MIS in the adult, including regulation of steroidogenesis. Mice chronically overexpressing a human MIS transgene develop varying degrees of gonadal abnormalities in the adult (Behringer et al., *Nature* 345:167–170 (1990)). Soon after birth, ovaries become depleted of germ cells and organize into structures resembling seminiferous tubules; later, the ovaries degenerate in the adult. Male mice (25%) from the highest MIS-overexpressing animals have undescended testes, which are also depleted of germ cells. These males lacked seminal vesicles and had underdeveloped epididymides, feminized external genitalia, and serum levels of testosterone 1/10th those in normal male mice (Behringer et al., *Nature* 345:167–170 (1990); Lyet et al., *Biol. Reprod.* 52:444–454 (1995)). These results suggested that MIS overexpression might interfere with androgen biosynthesis in Leydig cells. Conversely, homologous recombination in mice so that they no longer expressed either the MIS ligand (Behringer et al., *Cell* 79:415–425 (1994)) or the MIS type II receptor (Mishina et al., *Genes Dev.* 10:2577–2587 (1996)) also resulted in gonadal abnormalities consisting of Leydig cell hyperplasia and focal atrophy of the germinal epithelium. Thus, MIS appears to have a role in maintaining steroid hormone balance in both male and femal gonads after birth.

Leydig cells or intestinal cells are found in the testes surrounding the seminiferous tubules. Their major function is to produce testosterone, which is essential for the normal male phenotype. Testosterone is synthesized from cholesterol in five steps by the activity of four enzymes (FIG. 1), three of which the present inventors have studied: P450scc, P450c17, and 3β-hydroxysteroid dehydrogenate/$\Delta^5$-$\Delta^4$-isomerase (3βHSD)(Payne and Youngblood, *Biol. Reprod.* 52:217–225 (1995)). P450cc (cytochrome P450-side chain cleavage, also known as CYP11A) is a member of the superfamily of cytochrome P450 hemeproteins (Nelson et al., *DNA Cell Biol.* 12:1–51 (1993)), is located on the inner mitochondrial membrane, and catalyzes the committed steps of cholesterol conversion to steroid hormones by converting the 27-carbon cholesterol molecule to the 21-carbon pregnenolone. Pregnenolone moves out of the mitochondria and is converted to progesterone by the activity of 3βHSD, a nonP450 enzyme. Cytochrome P450c17α hydroxylase/$C_{17-20}$ lysase (P450C17, CYP17) has dual activities; it hydroxylates progesterone at the 17α position and converts the 21-carbon 17α-hydroxyprogesterone to the 19 carbon androstenedione. Androstenedione is then converted to testosterone by the activity of 17-ketosteroid reductase, a non-P450 enzyme the reduces the ketone at the carbon 17 position.

Recent studies have shown that the steady state levels of messenger RMAs (mRNAs) for steroidogenic enzymes P450scc, 3βHSD and P450C17 appear down-regulated in the testes and in purified Leydig cells of the MIS-overexpressing transgenic mice, as was the level of serum testosterone and estradiol (Racine et al., *Proc. Natl. Acad. Sci. USA* 95:594–599 (1998); Rouiller-Fabre et al., *Endocrinology* 139:1213–1220 (1998)). Correlative PT-PCR results showed that the MIS type II receptor mRNA was present in purified Leydig cells, suggesting that the MIS exterted its observed Leydig cell effects directly via the MIS receptor (Racine et al., *Proc. Natl. Acad. Sci. USA* 95:594–599 (1998)).

Signal transduction by members of the TGFβ family of glycoprotein homodimers occurs when the ligand binds to a heteromeric complex of single transmembrance, serine/threonine kinases. Ligand specificity within the family is determined by the type II receptor, which, in turn, recruits and phosphorylates the appropriate type I receptor for subsequent downstream signaling via subsets of ligand-specific Smads (Kretzschmar and Massague, *Curr. Opin. Genet. Dev.* 8:103–111(1998)). Efforts to determine the molecular mechanisms of MIS signal transduction have led us and others to the cloning of the MIS ligand and its MIS type II receptor and their characterization (Cate et al., *Cell* 45:685–698 (1986); Picard et al, *Proc. Natl. Acad. Sci. USA* 83:5464–5468 (1986); Baarends et al., *Development* 120:189–197 (1994); di Clemente, et al., *Mol. Endocrinol.* 8:1006–1020 (1994); Teixeira et al., *Endocrinology* 137:160–165 (1996)). To understand the downstream pathways that are activated by the MIS ligand binding to its receptor, we are dissecting the role that MIS plays in Leydig cell function and steroidogenesis. Using the rodent Leydig tumor cells lines R2C and MA-10, we have established a system for studying MIS signal transduction and have been able to show that MIS regulates steroidogenesis at the transcriptional level.

Having generally described the invention, the same will be more readily understood by reference to the following examples, which are provided by way of illustration and are not intended as limiting.

In the following examples, the materials and methods used are as follows.

Materials

Chemicals were obtained from Fisher Scientific (Fairlawn, N.J.) or Sigma Chemical Co. (St. Louis, Mo.) unless otherwise noted. Maymouth's MB752/1 medium, gentamicin, oligonucleotides, and trypsin-EDTA were obtained from Life Technologies, Inc. (Grand Island, N.Y.).

Restriction and modifying enzymes, firefly luciferase and Renilla luciferase vectors, and reagents were purchased from Promega Corp. (Madison, Wis.). Radionucleotides were purchased from New England Nuclear (Boston, Mass.). Rat P450scc complementary DNA (cDNA) was a gift from Dr. J. S. Richards (Baylor College of Medicine, Houston, Tx.). Female(fetal calf serum (FCS) was obtained from Aires Scientific/Biologos (Richardson, Tx.). Standard recombinant DNA techniques were used (Sambrook et al., *Molecular Cloning: A Laboratory Manual*, Cold Spring Harbor Laboratory Press, Cold Spring Harbor, N.Y. (1989)). Advantage polymerase enzyme was used in the PCR amplification (CLONTECH Laboratories, Inc., Palo Alto, Calif.). All animal studies were performed in accordance with the NIH Guide for the Care and Use of Laboratory Animals.

Cell Culture

R2C, a rat Leydig tumor cell line (American Type Culture Collection, Manassas, Va.), was maintained in F-10 medium containing 15% horse serum and 2.5% female FCS (Aires Scientific/Biologos). The mouse MA-10 Leydig rumor cell line, a gift from Dr. Mario Ascoli (University of Iowa, Ames, Iowa), was maintained in Waymouth's MB 752/1 medium (Life Technologies, Inc.) modified to contain 20 mm HEPES (pH 7.4), 50 µg/ml gentamicin, and 15% horse serum. For these experiments, R2C and MA-10 cells were incubated in a humidified atmosphere with 5% $CO_2$ at 37° C. and fed every other day until reaching 80–90% confluence.

Northern Analyses

Total RNA was extracted using the guanidine isothiocyanate-cesium chloride method (Sambrook et al., *Molecular Cloning: A Laboratory Manual*, Cold Spring Harbor Laboratory Press, Cold Spring Harbor, N.Y. (1989)). All RNA was extracted with successive rounds of phenol, chloroform, and ether; ethanol precipitated; and quantified by absorbance at $A_{260}$. Ten micrograms of each RNA sample were denatured with dimethylsulfoxide and glyoxal at 65° C., separated in a 1.5% agarose gel, blotted overnight onto nylon membranes, and either baked at 80° C. in a vacuum oven or UV cross-linked. Testes were surgically extracted from 30-day postnatal rats and homogenized, and RNA was extracted as before for use as a positive control. RNA from isolated primary Leydig cells of 21-day-old rats purified by Percoll density gradient centrifugation to 95% homogeneity was provided by Dr. Mary Lee (Lee et al, "Mullerian inhibiting substance type II receptor expression and binding in primary Leydig cells," *Endocrinology* (in press)). Blots were prehybridized with 100 µg/ml sonicated salmon sperm DNA in 50% formamide hybridization solution for 3 h at 65° C. for riboprobes and at 42° C. for random primed probes. The MIS type II receptor plasmid was linearlized with EcoRV and riboprobes made with 5P6 polymerase using standard techniques. $^{32}$P-Labeled random primed cDNA probes were made for P450cc and 3βHSD. Rat P450scc cDNA was a gift from Dr. J. S. Richards (Baylor College of Medicine). The P450c17 plasmid was linearized with EcoRI and the $^{32}$P-labeled riboprobe made with T7 RNA polymerase using standard techniques. Blots were hybridized overnight with $2\times10^6$ cpm/ml probe with riboprobes at 65° C. and washed at 72° C. with random primed human probes at 42° C. and washed at 60° C. with 0.1×SSC (1×SSC=150 mM sodium chloride and 15 mM sodium citrate)-0.1% SDS and exposed to radiographic film with intensifying screens at −70° C. for 3 days. All animal studies were performed in accordance with the NIH Guide for the Care and Use of Laboratory Animals, with institutional approval on Aug. 19, 1998 under accession no. 97-4216.

Radioimmunoassays

MA-10 cells were plated on day 0 in sextuplicate at $5\times10^4$/well in 12-well plates for each time point indicated. Recombinant human MIS (rhMIS) was prepared from Chinese hamster ovary (CHO) cells stable transected with a linear construct of the human MIS gene (Cate et al., *Cell* 45:685–698 (1986)). Active secreted protein in the growth medium was then passed over an immunoaffinity column prepared with the monoclonal MIS antibody, 6E11, conjugated to Affi-Gel-10 (Ragin, et al., *Protein Expr. Purif.* 3:236–245 (1992)). Bound MIS was then eluted off the column with 3M ammonium thiocyanate solution, pH 7.4, or 1M acetic acid, pH 3.0. Protein concentrations were determined by Bradford assays after pH neutralization and desalting by centrifugal filtration (Bradford, M. M., *Anal Biochem.* 72:248–254 (1976)). The bioactivity of the MIS was then verified using an established organ culture assay, which grades the regression of the 14.5-day gestation rate urogenital ridge (Donohoe et al., *J. Surg. Res.* 23:141–148 (1977)). Vehicle control or 105 nM MIS in the presence or absence of $(Bu)_2cAMP$ (50 µm) was added to MA-10 cells 2 days after plating and incubated for the indicated number of days. Culture medium was collected and assayed by RIA for total accumulated progesterone and testosterone by the NICHHD P30 Reproductive and Endocrine Sciences RIA Core Laboratory at the Massachusetts General Hospital.

Luciferase Reporter Assays

The P450c17 promoter fragment of 1018 bp was amplified by PCR from mouse genomic DNA using 5'-GAGCTCGAGTATTGGCATTGCGTCCC (SEQ ID NO:1) and 5'-CTCGAGGGCAGATGGCCAGCTGTGGA (SEQ ID NO:2) as primers with complimentary SacI and XhoI sites (Payne et al., *J. Steroid Biochem. Mol. Biol.* 43:895–906 (1992)). Advantage polymerase enzyme was used in the PCR amplification (CLONTECH Laboratories, Inc., Palo Alto, Calif.). The PCR fragment was cloned into pCRII (Invitrogen, San Diego, Calif.) for sequence analysis and cut out with SacI/XhoI. PGL3B vector was digested with SacI and XhoI and ligated to the P450c17 promoter fragment, generating P450c-17-Luc. The constructs were purified by cesium chloride ultracentrifugation. MA-10 cells were plated at $2\times10^5$ in triplicate and were transfected with P450c-17-α-Luc using the FuGene 6 lipid protocol (Roche Molecular Biochemicals). PGL3B, the promoterless patent plasmid was used as a negative control. pRL-TK encoding Renilla luciferase (Promega Corp.) under the control of a HSV thymidine kinase promoter was cotransfected as an internal control for transfection efficiency and steroid pathway specificity. Cell lysates were made and assayed for luciferase activity using a Berthold Automatic luminometer (Mallac, Inc., Turku, Finland).

EXAMPLE 1

The MIS Type II Receptor Is Expressed in Leydig Cells

Figure 2:
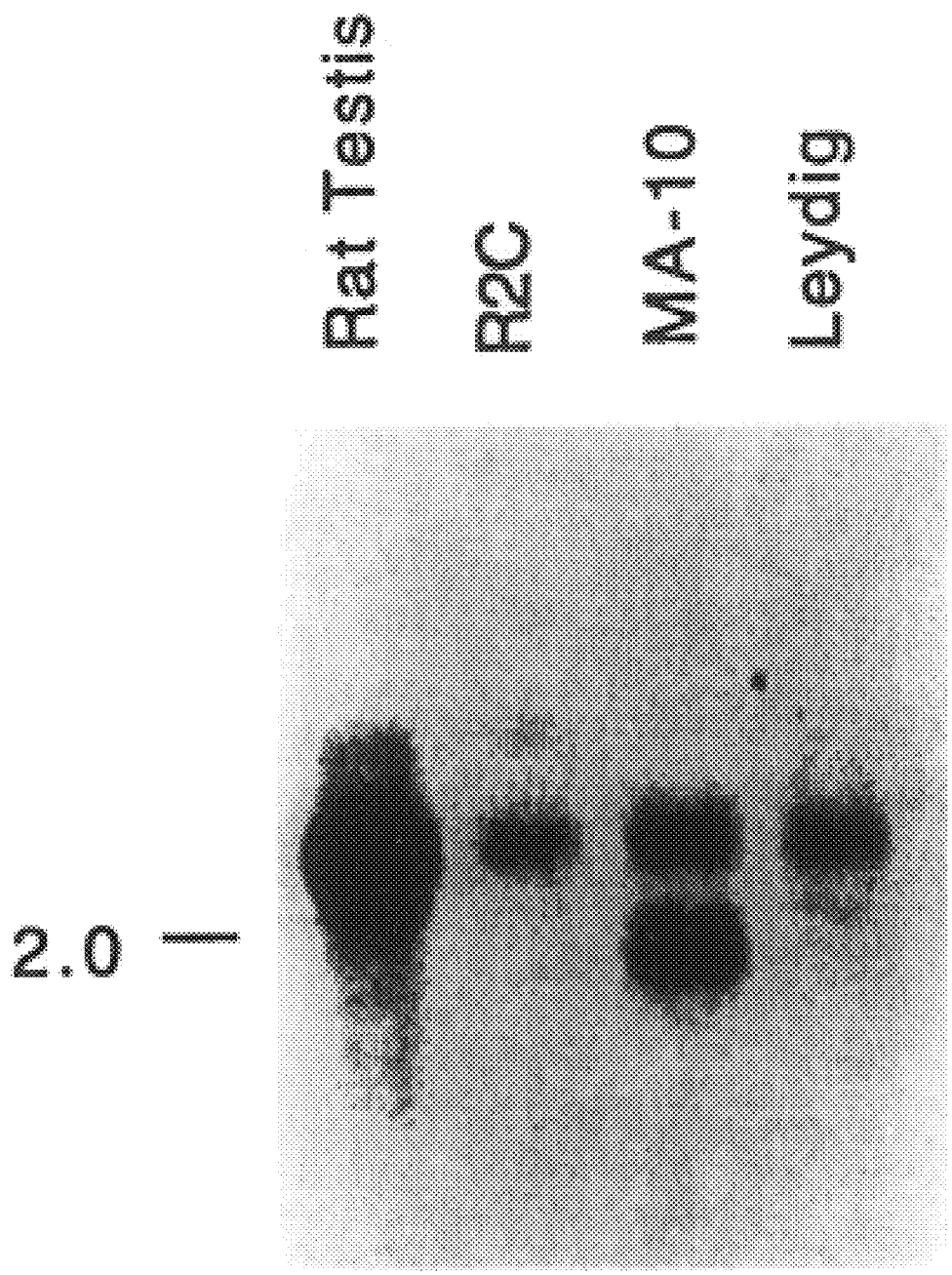
FIG. 2 depicts results of a study of MIS type II receptor mRNA expression in rodent Leydig cells. Total RNA was isolated from the indicated sources, denatured, electrophoresed, bloated to a nylon membrane, and probed with a radio-labeled MIS type II receptor riboprobe. The blot was exposed to x-ray film to detect the migration of hybridized mRNA. The mol. wt. marker shown indicates the migration of the 2-kb band of a λHindIII digest.

The MIS ligand binds to the MIS type II receptor to initiate downstream signaling. Northern analysis (see FIG. 2) was performed to determine whether there was requisite expression of the MIS type II receptor in total RNA isolated from rat testes, R2C cells, MA-10 cells, and purified primary Leydig cells. These findings indicate that Leydig cells could respond directly via the MIS type II receptor from paracrine production of MIS in the nearby Sertoli cells. The bands observed under stringent hybridization conditions in the cell lines and purified Leydig cells migrated a distance equal to that seen with testis RNA, suggesting that the MIS type II receptor probe hybridized to the same mRNA species.

MA-10 cells show a faster migrating band than that seen with R2C cells in other Northern experiments.

EXAMPLE 2

MIS Inhibits Steroid Production by Leydig Cells

To determine whether MA-10 would serve as suitable cells in which to study the down-regulation of steroid hormone production observed in mice overexpressing MIS in vivo, MA-10 were incubated with MIS and the levels of progesterone and testosterone secreted into the medium was measured (FIGS. 3A and 3B). MA-10 cells are a mouse Leydig cell tumor line that, in addition, have functional gonadotropin receptors resulting in enhanced steroid production in response to cAMP or LH/hCG, thus mimicking the physiological state of Leydig cells in vivo (Payne and Youngblood, *Biol. Reprod.* 52:217–225 (1995); Ascoli, M., *Endocrinology* 108:88–95 (1981)).

FIG. 3A shows that incubation of MA-10 cells with MIS for 2 days resulted in a modest, but significant, 40% reduction in progesterone secretion in both the cAMP-stimulated and unstimulated states. FIG. 3B shows the concentration of testosterone secreted by MA-10 cells incubated with MIS over a 2-day time course was 10-fold lower than that of cells not treated with MIS. The level and time course of steroid hormone reduction were similar to those seen when human follicular cells, harvested at the time of in vivo fertilization, were incubated with recombinant MIS (Kim et al., *J. Clin. Endocrinol. Metab.* 75:911–917 (1992)) and when primary Leydig cells were incubated with MIS (Rouiller-Fabre et al., *Endocrinology* 139:1213–1220 (1998)).

EXAMPLE 3

MIS Reduces Steady State Levels of c17 mRNA

Figure 4A:
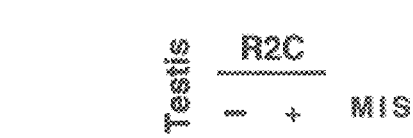
FIGS. 4A–C depict a Northern analysis of the expression of RNAs for steroidogenic enzymes. Northern analysis of the steady state levels of mRNAs from the indicated cells for steroidogenic enzymes was performed as described in Materials and Methods with the indicated probes. Blots were reprobed with a human β-actin to control for sample loading.
Figure 4A:
Figure 4A:
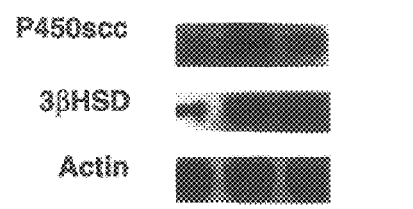
Figure 4B:
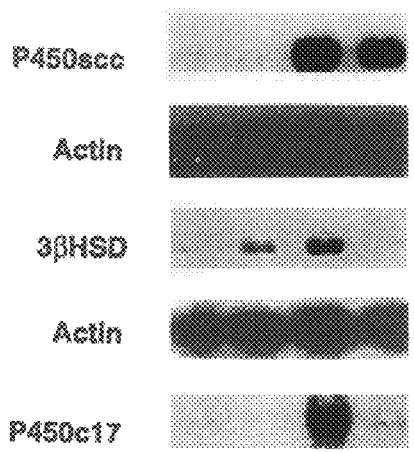
Figure 4C:

To uncover the molecular mechanisms responsible for these effects, the effect of MIS on the steady state levels of the mRNAs for the steroidogenic enzymes P450scc, 3βHSD, and P450c17 were examined (FIGS. 4A–C). Northern analysis revealed that the levels of mRNA, although marginally lower for P450scc and 3βHSD for both R2C after 3-h treatment and MA-10 cells after overnight treatment with MIS (FIGS. 4A and 4B, respectively), were dramatically reduced for P450c17 to undetectable levels in cAMP-stimulated MA-10 cells.

We also tested whether the down-regulation of c17 MRNA by MIS required protein synthesis, which would indicate whether the effect of MIS on c17 mRNA was direct and found that overnight incubation of MA-10 cells with MIS in the presence of cyclohexamide, a protein synthesis inhibitor, continued to cause a significant decrease in the steady state level of c17 mRNA (FIG. 4C). RNA was prepared from MA-10 cells, incubated with MIS in the presence or absence of cyclohexamide and analyzed by Northern blot for c17 mRNA. Surprisingly, addition of cyclohexamide alone was sufficient to induce expression of c17 mRNA above levels seen with cAMP induction.

EXAMPLE 4

MIS Regulates c17 Expression at the Transcriptional Level

Changes in mRNA for the steroidogenic enzymes could be reflected in, among others, differences in message stability, nuclear export, or transcription, all of which could be potential points for regulation by MIS. To study transcriptional regulation of the Cyp17gene by MIS, DNA constructs were made containing approximately 1 kb of the Cyp17 promoter fused with the firefly luciserase gene, transfected them into MA-10 cells, and assayed for luciferase activity (FIGS. 5A–C). In the first set of experiments, on the day after transfection with the reporter construct, MA-10 cells were incubated with varying concentrations of MIS and harvested either 18 or 29 h later to permit induction of luciferase activity, which was measured and compared (FIG. 5A). MIS appears to exert its effect on the exogenous Cyp17 promoter/luciferase reporter after only 18 h with 70 nM MIS. By 29 h, 35 nM MIS was able to markedly lower luciferase activity and, with 105 nM MIS, luciferase activity was reduced to background levels. These concentrations, which are high compared with those required for transcriptional activation by other members of the TGFβ family, are similar to those required for an MIS effect in other assays and with the 35- nM MIS concentration required for complete regression of the Mullerian duct in the organ culture bioassay used to test the potency of MIS preparations (Racine et al., *Proc. Natl. Acad. Sci. USA* 95:594–599 (1998)s; MacLaughlin et al., *Methods Enzymol.* 198:358–369 (1991)). Also, firefly luciferase activation is normalized to a cotransfected Renilla reporter to rule out nonspecific effects on the cell by MIS. It is also important to note that the MIS preparations were tested and were found to be free of activin and TGFβ by enzyme-linked immunoabsorbant assay, and that when TGFβ was added to MA-10, the Cyp17-driven luciferase activity was not significantly different from that of untreated cells (not shown).

FIG. 5B shows that MIS incubation on the day after transfection has a slight, but significant, effect on luciferase after 3 h and becomes pronounced after 18 h. In another experiment, MA-10 cells when incubated with L9, an inactive form of the MIS ligand that has been mutated so that pro-MIS could not be cleaved to generate the bioactive C-terminal portion of the hormone (MacLaughlin et al., *Endocrinology* 131:291–296 (1992)), did not affect luciferase activity as did bioactive, cleavable MIS at the same concentration and time (shown with an asterisk in FIG. 5B). As L9 is produced in CHO cells and purified in the same manner as wild-type MIS, we can conclude that the effect on P450c17 transcription is due to MIS and not to a possible copurified contaminant.

Luciferase expression appears maximal after overnight transfection, as luciferase activity was not significantly different in the control MA-10 cells with 3- to 18-h additional incubation (FIG. 5B). To take advantage of an earlier MIS effect, we transfected the Cyp17 reporter construct and added MIS at the same time. As shown in FIG. 5C, 18 h after transfection, we observed a 4-fold decrease in luciferase activity with added MIS, which is considerably greater than that observed when MIS was added 1 day later. This observation suggests that MIS can more effectively repress expression of the Cyp17 promoter-driver reporter before it is fully activated.

In human males, after the first year of life there is a reciprocal relationship between expression of MIS and serum testosterone concentrations that remains throughout life (Bardin et al., "Androgens," in *Reproductive Endocrinology, Surgery and Technology*, Adashi et al., eds., Lippincott-Raven, Philadelphia (1995), pp. 505–525; Josso et al., *Early Hum. Dev.* 33:91–99 (1993); Lee et al., *J. Clin. Endocrinol. Metab.* 81:571–576 (1996)). During fetal life and again after the testosterone nadir in the immediate perinatal period, however, both MIS and testosterone levels are high. At birth, the levels of MIS in males are slightly lower, but still 10-fold higher than those in females. During the first 6 months of life (minipuberty), there is a sharp peak in serum testosterone and a gradual increase in MIS concentration to its highest level, which is reached by the first 12 months of age when the concentration of serum testosterone in males is again at a low point. In precocious puberty syndromes, such as occurs with testotoxicosis or in the McCune-Albright syndrome, testosterone levels are elevated at an early age. Testotoxicosis is caused by activating mutations in the stipulatory G protein-coupled receptor (that are usually due to somatic mutations during early embryonic development) are responsible for the McCune-Albright syndrome (Yen et al., *Reproductive Endocrinology: Physiology, Pathophysiology, and Clinical Management*, Saunders, Philadelphia (1999), pp. viii 839). As serum MIS and testosterone concentrations are inversely related during normal and precocious puberty, others have speculated that androgens regulate MIS expression (Rey et al., *J. Clin. Endocrinol. Metab.* 77:1220–1226 (1993)). However, attempts to simulate androgen-regulated MIS expression in tissue culture (Happ and P. K. Donahoe, unpublished) have not been fruitful, and thus the hypothesis remains speculative.

We have observed an effect of MIS on progesterone secretion by MA-10 cells that was reflected in a decrease in steady state mRNA levels for both P450scc and 3βHSD.

MIS regulation of steroidogenesis in Leydig cells by transcrptional control of Cyp 17 exposes a conundrum in MIS-mediated suppression of testosterone synthesis that may indicate is developmentally regulated. Fetal Leydig cells proliferate and show increased androgen synthesis, which is required for male phenotypic development, independent of gonadotropin stimulation in the rodent (O Shaughnessy et al., Endocrinolo gy 139:1141–1146 (1998), Kendall et al., Genes Dev. 9:2007–2019 (1995)). We would have expected that these fetal Leydig cells must be refractory to MIS-mediated inhibition of androgen synthesis, because the level of MIS is also high at this time. However, in MIS-overexpressing mice (Behringer et al., Nature 345:167–170 (1990)) impairment of the testosterone-regulated differentiation of the fetal Wolfian duct, which is the precursor of the vas deferens, epididymides, and seminal vesicles, was observed. Also, incubation of fetal rat Leydig cells with MIS in vitro results in suppression of testosterone synthesis (Rouiller-Fabre et al., Endocrinology 139:1213–1220 (1998)). After birth, when MIS levels remain high, fetal-derived Leydig cells begin regressing, and lower levels of androgens ensue. The adult Leydig cells arise and proliferate from mesenchyme precursors at puberty, when MIS levels reach their nadir (Lee et al., *J. Clin. Lndocrinol. Metab.* 81:571–576 (1996); Hudson et al., *J. Clin. Endocrinol. Metab.* 70:16–22 (1990)), and begin producing androgens after stimulation with LH (Saez, J. M., Endocr. Rev. 15:574-626 (1994)). The MIS-regulated cell lines used in our studies were originally derived from this adult Leydig cell population. This distinction is important when attempting to understand why fetal Leydig cells, which are in an environment with high levels of MIS, continue to produce androgens.

Although the amount of testosterone secreted by MA-10 cells is much lower than that secreted by purified Leydig cells (Rouiller-Fabre et al., *Endocrinology* 139:1213–1220 (1998)) and significantly lower than the level of progesterone, prevailing opinion is that MA-10 cells do not produce testosterone. Our results clearly indicate not only that MA-10 cells secrete measurable amounts of testosterone into the medium, but that it can be enhanced 3-fold by cAMP addition. The original report detailing the cloning and characterization of the MA-10 cell line also shows low levels of testosterone secretion, which was induced with hCG. MA-10 cells have proven enormously valuable to understand MIS-mediated inhibition of Cyp17 expression and will be very useful in our future efforts to understand the molecular mechanisms of that inhibition.

In our studies to determine whether the MIS signal transduction directly mediated suppression of Cyp17 mRNA expression in the absence of protein synthesis, we observed that Cycloheximide alone was able to induce expression of Cyp17 mRNA. The increase in Cyp17 mRNA with cyclohexamide treatment is probably not artifactual and is commonly observed with labile mRNAs (Theodorakis and Cleveland, in *Translation Control*, Hershey et al., eds., Cold Spring Harbor Laboratory Press, Cold Spring Harbor, N.Y. (1996), pp. 631–652); it could indicate the presence of a protein that inactivates or turns over a crucial component of Cyp17 expression. In the case of c-myc mRNA, mRNA stability has been linked to translation of the c-myc mRNA itself, i.e., c-myc mRNA decay is accelerated by its translation. Cyclohexamide blocks c-myc translation and therefore prolongs the c-myc MRNA half-life (Yeilding et al., *J. Biol. Chem.* 273:15749–15757 (1998)).

Many advances in understanding TGFβ signal transduction mechanisms have been made because of the availability of both a cell line that responds to TGFβ and a reporter gene with which to measure that response. Until now such a model system for studying MIS signal transduction has been lacking. Evidence of transcriptional regulation of steroidogenic enzymes in rodent Leydig cells by MIS is a significant advance in our understanding of MIS signal transduction. This first example of transcriptional regulation of a gene by MIS can be used to advantage to dissect and define the relevant MIS-specific cis-elements and trans-acting factors and the upstream pathways that are responsible for MIS receptor-mediated molecular events.

There are a number of potential clinical implications that could emanate from the study of this MIS signal transduction pathway. For example, MIS-specific checkpoints in the MIS-mediated down-regulation of testosterone synthesis could be activated and used to lower endogenous testosterone in such clinical settings as prostatic cancer and benign prostatic hypertrophy or to lower elevated steroids in precocious puberty syndromes. Current treatments with GnRH long acting analogs to down-regulate the GnRH receptor have been successful in the treatment of central precocious puberty (Hoffman and Crowley, *N. Engl. J. Med.* 307:1237–1241 (1982)), but it is the downstream variants for which treatment is not yet optimal and could be augmented by MIS-related treatments. Over 60% of McCune-Albright patients, who for unknown reasons have a 31 ratio of females to males, have elevated sex steroids in the absence of elevated gonadotropins due to activating mutations in the α-subunit of the G protein-regulating adenylyl cyclase (Ringel et al., *Medicine* 75:171–184 (1996)). In these patients with gonadotropin-independent precocious puberty, suppression of multiple enzymes in the steroid production pathway by MIS might, for example, be used to augment the currently used aromatase inhibitor, which have been helpful over the short term, but less effective over the long term (1–3 yr.) (Feuillan et al., *N. Engl. J. Med.* 315:1115–1119(1986);Hauffa et al., *Helv. Paediatr. Acta* 42:471–480 (1987)).

EXAMPLE 5

MIS Regulates Testosterone In Vivo

Figure 6:
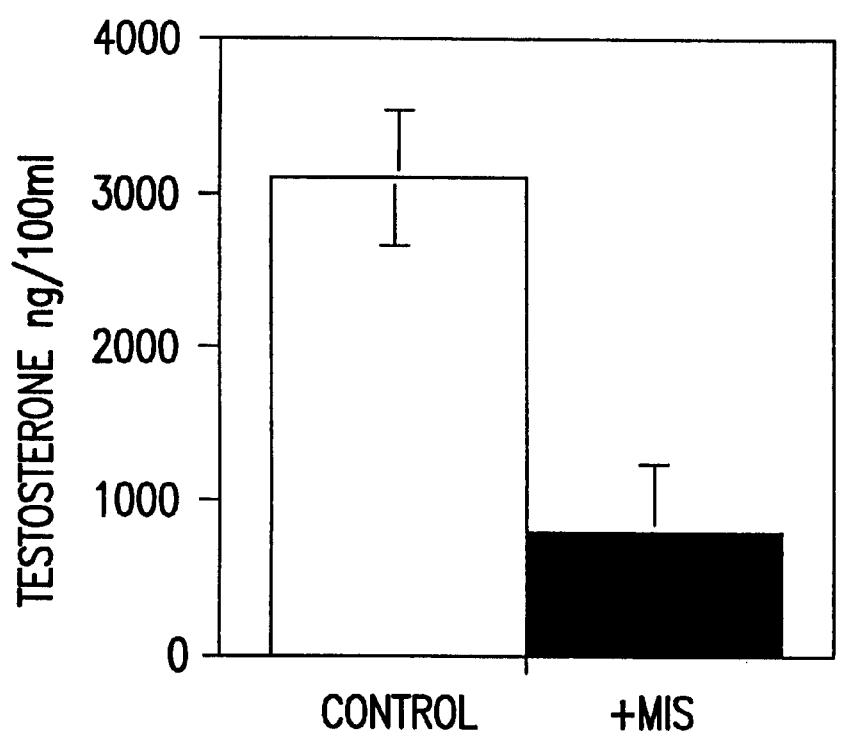
FIG. 6 depicts the results of a study of MIS regulation of testosterone concentration iv vivo. Adult male rats (250 g) were administered either hCG (50 U, n=3, white bar), or 50 U hCG and 1 mg MIS (n=3, black bar) intraperitoneally. After 18 hours, serum was collected from each of the animals and tested for testosterone concentration using a radioimmunoassay. The mean values in each group are shown, and error bars represent SEM, $p<.0.05$.

Adult male rats (250 g) were administered either hCG (50 U, n=3, white bar), or 50 U hCG and 1 mg MIS (n=3, black bar) intraperitoneally. After 18 hours, serum was collected from each of the animals and tested for testosterone concentration using a radioimmunoassay. The results are shown in FIG. 6. The mean values in each group are shown, and error bars represent SEM, p<.0.05. These data show that serum testosterone is lowered by MIS administration.

EXAMPLE 6

Acute Administration of MIS Regulates Testosterone In Vivo

To study the acute regulation of steroids, LH or hCG, with or without rhMIS, is administered to animals by intraperitoneal injection. At six time points (10 animals each), animals are injected intraperitoneally with LH (25 IU) with or without MIS in a single injection. At the inidcated times (30 min, 1 h, 2 h, 4 h, 8 h, 18 h), blood is collected for measurement of serum MIS, LH and testosterone, and the testes are harvested for preparation of RNA and for histology. mRNA expression of steroidogenic enzymes (SCC, 3βHSD, Cyp17, etc.) is analyzed by Northern analysis. rhMIS suppresses serum testosterone concentration.

EXAMPLE 7

Long-Term Administration of MIS Regulates Testosterone In Vivo

To study the long term regulation of steroids, LH or hCG, with or without rhMIS, is administered to animals via Alzet osmotic minipumps. The effects of chronic MIS exposure is analyzed daily for one week. LH levels are measured, since low testosterone will elevate LH, which in turn could increase the testosterone concentration, to compensate for and possibly obscure an MIS effect. Conversely, LH or cAMP and subsequently high testosterone levels may be required to observe the MIS inhibitory effects, as with the cAMP stimulation of MA-10 cells in vitro. If LH is found to compensate for the MIS effect in vivo, the studies are repeated, in either hypophysectomized rats or animals physiologically clamped with a long acting LHRH analog, with subsequent carefully controlled hCG or LH delivery prior to MIS treatment. rhMIS suppresses serum testosterone concentration.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method of treating a condition or disease characterized by an excess of one or more androgens relative to a normal level, said method comprising administering an effective amount of MIS to a patient.

2. The method of claim 1, wherein said one or more androgens is testosterone.

3. The method of claim 1, wherein said MIS has a molecular weight of about 140 kDa or about 70 kDa.

4. The method of claim 1, wherein said MIS is the C-terminal fragment of MIS.

5. The method of claim 3, wherein said C-terminal fragment has a molecular weight of about 25 kDa or about 12.5 kDa.

6. The method of claim 1, wherein said condition or disease is selected from the group consisting of polycystic ovarian disease and precocious puberty.

7. The method of claim 6, wherein said condition or disease is polycystic ovarian disease.

8. The method of claim 6, wherein said condition or disease is precocious puberty.

9. A method of decreasing the plasma level of one or more androgens, said method comprising administering to a patient an effective amount of MIS, wherein said amount of MIS is sufficient to decrease the plasma level of said one or more androgens below the normal level for said one or more androgens.

10. The method of claim 9, wherein said one or more androgens is testosterone.

11. The method of claim 9, wherein said MIS has a molecular weight of about 140 kDa or about 70 kDa.

12. The method of claim 9, wherein said MIS is the C-terminal fragment of MIS.

13. The method of claim 12, wherein said C-terminal fragment has a molecular weight of about 25 kDa or about 12.5 kDa.

14. The method of claim 9, wherein said patient has benign prostatic hypertrophy, and wherein as a result of the administration of said MIS, the extent of said hypertrophy is diminished.

15. The method of claim 9, wherein said patient has prostate cancer, and wherein as a result of the administration of said MIS, the progression of said cancer is halted or slowed.

* * * * *